United States Patent [19]

Ueeda

[11] 4,003,920

[45] Jan. 18, 1977

[54] METHOD FOR PRODUCING MALEIC ANHYDRIDE USING A PROMOTED TUNGSTEN, PHOSPHOROUS OXIDE CATALYST

[75] Inventor: Ryuhei Ueeda, Kurashiki, Japan

[73] Assignee: Kuraray Co., Ltd., Kurashiki, Japan

[22] Filed: Nov. 30, 1973

[21] Appl. No.: 420,742

Related U.S. Application Data

[63] Continuation-in-part of Ser. No. 301,933, Oct. 30, 1972, Pat. No. 3,906,008.

[30] Foreign Application Priority Data

| Dec. 4, 1972 | Japan | 47-121865 |
|---|---|---|
| Dec. 4, 1972 | Japan | 47-121866 |
| Dec. 4, 1972 | Japan | 47-121867 |
| Dec. 4, 1972 | Japan | 47-121868 |

[52] U.S. Cl. .................. 260/346.8 A; 260/533 R; 252/435; 252/437
[51] Int. Cl.² ..................................... C07D 307/60
[58] Field of Search ............................ 260/346.8 A

[56] References Cited

UNITED STATES PATENTS

| 3,156,705 | 11/1964 | Kerr ............................ 260/346.8 |
| 3,296,282 | 1/1967 | Kerr ............................ 260/346.8 |
| 3,478,063 | 11/1969 | Friedrichsen et al. ........ 260/346.8 |
| 3,906,008 | 9/1975 | Ueeda ......................... 260/346.8 |

FOREIGN PATENTS OR APPLICATIONS

| 1,601,955 | 10/1970 | France ......................... 260/346.8 |
| 47-34313 | 11/1972 | Japan .......................... 260/346.8 |

*Primary Examiner*—Natalie Trousof
*Assistant Examiner*—Bernard Dentz
*Attorney, Agent, or Firm*—Kramer & Brufsky

[57] ABSTRACT

Maleic anhydride is obtained by oxidizing an unsaturated hydrocarbon having at least 4 carbon atoms in the presence of a catalyst comprising the oxides of tungsten and phosphorus, and at least one catalyst promoter selected from the groups consisting of a compound of a metallic element belonging to groups III A, III B, IV A and VIII of the Periodic Table; arsenic, zirconium, antimony, and niobium.

10 Claims, No Drawings

METHOD FOR PRODUCING MALEIC ANHYDRIDE USING A PROMOTED TUNGSTEN, PHOSPHOROUS OXIDE CATALYST

This application is a continuation-in-part of Ser. No. 301,933 filed Oct. 30, 1972, and now U.S. Pat. No. 3,906,008.

This invention relates to a method for producing maleic anhydride by oxidizing an unsaturated hydrocarbon having at least 4 carbon atoms or a hydrocarbon mixture containing such unsaturated hydrocarbons with oxygen or a gaseous mixture containing oxygen.

It is well known that maleic anhydride can be produced by oxidizing an unsaturated hydrocarbon having at least 4 carbon atoms in the presence of a catalyst comprising vanadium oxide. However, when vanadium oxide is used as a catalyst, the yield of maleic anhydride is fairly low. In order to improve the yield of maleic anhydride when using a catalyst comprising vanadium oxide, co-catalysts such as molybdenum oxide, tungsten oxide and phosphorus oxide are generally added to the catalyst. For example, a catalyst comprising vanadium pentoxide and oxides of phosphorus and tungsten is described in Japanese Patent Publication No. 9688/62. In that case, however, the yield of maleic anhydride is still unsatisfactory.

It has been proposed that, by using tungsten as a catalyst component and phosphorus as a co-catalyst component, i.e., by using a catalyst system consisting essentially of the oxides of tungsten and phosphorus, it is possible to achieve high yields of maleic anhydride and to inhibit the formation of by-products such as acetic acid and aldehyde compounds. Surprisingly, it has been found that, when a vanadium compound which is generally used as the catalyst for the production of maleic anhydride is added to the catalyst system comprising oxides of tungsten and phosphorus, the resultant catalytic activity is unexpectedly hindered and the yield of maleic anhydride decreases. However, these prior catalysts have the disadvantage of decreasing the catalytic activity during the reaction.

It has now been found according to the present invention that it is possible to obtain maleic anhydride in high yields and without a decrease in the catalytic activity during the reaction if there is added to the catalyst system consisting essentially of the oxides of tungsten and phosphorus, at least one catalyst promoter selected from the group consisting of a compound of a metallic element belonging to groups III A, III B, IV A, and VIII of the Periodic Table; arsenic, zirconium, antimony, and niobium.

It has been found that it is possible to obtain maleic anhydride in high yields and without a decrease in the catalytic activity during the reaction by introducing a phosphorus compound into the reaction zone.

Catalyst systems comprising oxides of tungsten and phosphorus which are useful in the present invention include (1) mixtures containing an oxide of tungsten and an oxide of phosphorus, (2) complexes or compounds of tungsten, phosphorus and oxygen and (3) mixtures thereof. It is desirable that the atomic ratio of tungsten to phosphorus (W/P) be less than 30, and preferably range from 1 to 18.

In order to prepare the catalysts used in accordance with the present invention, there can be employed (1) a tungsten compound preferably selected from the group consisting of $WO_3$, $H_2WO_4$, $H_4WO_5$, $(NH_4)_2WO_4$, $W_4O_{11}$, $W_{10}O_{29}$, $WCl_6$, $WBr_6$, $WCl_5$, $WBr_5$, metatungstic acid, ammonium metatungstate, ammonium paratungstate, alkali metal tungstate, alkaline earth metal tungstate and the like; (2) a phosphorus compound preferably selected from the group consisting of phosphorus pentoxide, hydrophosphorous acid, phosphorous acid, diphosphorous acid, hypophosphoric acid, orthophosphoric acid, metaphosphoric acid, ultraphosphoric acid, an ammonium salt of phosphorous or phosphoric acid, and the like; (3) at least one catalyst promoter selected from the oxides, hydroxides, chlorides, carbonates, sulfates, nitrates, phosphates, acetates, and the like of an element belonging to the groups III A, III B, IV A, and VIII of the Periodic Table; arsenic, zirconium, antimony and niobium. There can also be used compounds comprising by nature tungsten and phosphorus such as phosphotungstic acid or a salt thereof. When the catalyst promoter is employed in the catalyst comprising oxides of phosphorus and tungsten, it is desirable that the atomic ratio of the metal to phosphorus (metal/phosphorus) in the catalyst is in the range of from about 0.001 to 100.

When the aforementioned metal compounds are used in the form of chlorides or sulfates, chlorine or sulfate residues can remain in the catalyst. However, the presence thereof has no effect on catalytic activity.

In the present invention, phosphorus compounds can be introduced into the reaction zones by the following methods to maintain the high yield of maleic anhydride over extended periods: (1) a method wherein a phosphorus compound is added continuously or intermittently into the gaseous feed mixture, (2) a method wherein a phosphorus compound is introduced into the reaction zone with or without an inert gas such as steam, and (3) a method wherein a phosphorus compound is dissolved in a solvent such as water and is applied to the catalyst comprising oxides of tungsten and phosphorus during or after the reaction.

Typical phosphorus compounds which can be used include phosphine, phosphorus oxide (preferably phosphorus pentoxide), hydrophosphorous acid, phosphorous acid, diphosphorous acid, hypophosphoric acid, orthophosphoric acid, metaphosphoric acid, the salts of phosphorous or phosphoric acid which can be decomposed with heat such as ammonium dihydrogenphosphate, triethyl ammonium phosphate and organophosphorus compound preferably selected from the group consisting of

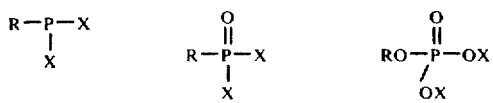

where R is phenyl or a lower alkyl radical and X is hydrogen or R, suitable compounds including for example diethyl phosphine, triethyl phosphine, tripropyl phosphine oxide, triethylphosphate and triphenyl phosphate.

Typical methods for producing the catalyst are described below.

A tungsten compound, for example, is first calcined in an air stream at a temperature of 400° to 1000° C for 1 to 20 hours to obtain a tungsten oxide. Then, the tungsten oxide is mixed with phosphoric acid diluted with an adequate quantity of water and a catalyst promoter as described hereinabove, and then the mixture is heated to obtain a pastelike mixture. By molding the pastelike mixture to a desired size and drying, a catalyst can be obtained. Further, by calcining the thus obtained catalyst at a temperature of 300° to 800° C, preferably 500° to 700° C, more stable and active catalysts can be prepared.

The oxides of phosphorus and tungsten, and a catalyst promoter as described hereinabove, which form the catalysts of the present invention can be supported on a carrier. In such case, supported catalyst systems can be obtained by the following method. After a molded carrier is dipped into an aqueous solution containing a tungsten compound or after a powdered carrier and tungsten are mixed and then molded into a desired size, the molded material is then calcined at an elevated temperature, and then the material is dipped into an aqueous solution containing a phosphorus compound and an aqueous solution containing a catalyst promoter as described hereinabove at the same time or separately. The supported catalyst obtained by such a method can be used in situ in the reaction. It can, of course, be used after being calcined. Conventional carriers can be employed such as silica gel, alumina, diatomaceous earth, alundum, carbolundum, calcium sulfate, and the like.

Typical of the unsaturated hydrocarbons containing at least 4 carbon atoms which can be used as feed materials according to the present invention include, for example, butene-1, butene-2, butadiene, cyclopentadiene, pentene-1, $C_4$-fractions obtained by naphtha cracking, and the like. It is possible to use mixtures of unsaturated hydrocarbons and hydrocarbon streams containing such unsaturated hydrocarbons therein in the present invention.

When preparing maleic anhydride, the oxidizing agent employed can be oxygen or a gaseous mixture containing oxygen such as air in admixture with the aforementioned unsaturated hydrocarbon. It is also possible to use, as an oxidizing agent, oxygen mixed with an inert gas such as nitrogen, carbon dioxide, steam, and the like. Furthermore, it is possible to use a dilute oxygen stream such as a portion of a reaction outlet gas stream containing oxygen. The concentration of unsaturated hydrocarbons in a reaction gaseous mixture varies widely according to the species of the unsaturated hydrocarbon and the inert gas used for dilution. Generally, the molar ratio of unsaturated hydrocarbon to oxygen is less than about 1/10 or more than about ½ in order to prevent explosions.

In order to produce maleic anhydride in accordance with the present invention, a catalyst containing oxides of phosphorus and tungsten, and a catalyst promoter as described hereinabove is packed into a reaction zone, and then a gaseous mixture containing an unsaturated hydrocarbon and oxygen or oxygen-containing gas is introduced into the reaction zone. It is desirable that the gaseous hourly space velocity (S.V.) of the gaseous feed mixture be in the range of from 100 to 15,000 per hour, preferably from 1500 to 9000 per hour. It is desirable that the temperature, which is highest in the catalyst layer, range from 250° to 650° C and preferably from 350° to 500° C.

In the present invention, the catalyst can be used in the form of a fixed bed, a fluidized bed or a moving bed. It is preferable to use the catalyst in a fluidized bed or a moving bed, because the reaction for producing maleic anhydride is exothermic.

The invention will be described in more detail by the following examples which are intended only to illustrate the invention. Unless otherwise stated, all percentages and parts are by weight. In these examples, the terms of conversion, selectivity for maleic anhydride and yield are defined by the following equations:

$$\text{conversion} = \frac{\text{moles of reacted unsaturated hydrocarbon}}{\text{moles of unsaturated hydrocarbon charged to reactor}} \times 100$$

$$\text{selectivity} = \frac{\text{moles of maleic anhydride formed}}{\text{moles of unsaturated hydrocarbon reacted}} \times 100$$

$$\text{yield} = \text{conversion} \times \text{selectivity}$$

EXAMPLE 1

50 grams of tungstic acid was calcined in an air stream at a temperature of 800° C for 3 hours. 45 grams of the thus obtained tungstic oxide were mixed with an aqueous mixture containing 7 grams of phosphoric acid having a purity of 85% and 2.4 grams of gallium nitrate octahydrate to obtain a pastelike mixture. The pastelike mixture was molded, and then dried. The thus obtained catalyst had an atomic ratio of phosphorus: tungsten: gallium (P:W:Ga) of 1:3.2:0.1. The catalyst was further calcined in an air stream at a temperature of 500° C for 2 hours before using in reaction.

The catalyst obtained by the aforementioned procedures was packed into a reactor having an inner diameter of 20 millimeters and a length of 60 centimeters. Keeping the highest temperature in the catalyst layer at 460° C, air containing one volume percent of butene-1 was introduced into the reactor at a space velocity of 3000 per hour. The results are shown in Table 1.

Table 1

| Lapse of Time After Start of Reaction (hour) | Conversion of butene-1 (%) | Maleic Anhydride | Yield (%) Carbon Monoxide | Carbon Dioxide | Acetic Acid | Aldehyde Compounds |
|---|---|---|---|---|---|---|
| 3 | 97 | 60 | 22 | 12 | 1 | 2 |
| 15 | 97 | 61 | 23 | 10 | 1 | 2 |
| 60 | 96 | 58 | 25 | 9 | 1 | 3 |

EXAMPLE 2

45 grams of tungsten oxide which were obtained by the same procedures as in Example 1 was mixed with an aqueous mixture containing 7.0 grams of phosphoric acid having a purity of 85% and 1.8 gram of scandium nitrate tetrahydrate to obtain a pastelike mixture. The pastelike mixture was molded, and then dried. The thus obtained catalyst had an atomic ratio of phosphorus: tungsten: scandium (P:W:Sc) of 1:3.2:0.1. The catalyst was further calcined in an air stream at a temperature of 500° C for 3 hours. Using the thus obtained catalyst, the same reaction procedures as in Examle 1 were repeated. The results are shown in Table 2.

Table 2

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 95 | 65 | 23 | 5 | 0 | 2 |
| 15 | 92 | 63 | 21 | 5 | 1 | 2 |
| 60 | 92 | 63 | 22 | 4 | 1 | 2 |

EXAMPLE 3

45 grams of tungsten oxide produced by the same procedure as in Example 1 was mixed with an aqueous mixture containing 7.0 grams of phosphoric acid having a purity of 85% and 23.2 gram of yttrium nitrate hexahydrate to obtain a pastelike mixture. The pastelike mixture was subjected to the same treatments as in Example 1 to produce a catalyst. The catalyst had an atomic ratio of phosphorus: tungsten: yttrium (P:W:Y) of 1:3.2:1. Using the catalyst, the same reaction procedure as in Example 1 was repeated. The deterioration in yield of maleic anhydride with time is shown in Table 3.

Table 3

| Lapse of time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compound |
| 3 | 97 | 60 | 24 | 9 | 1 | 3 |
| 15 | 98 | 64 | 25 | 5 | 1 | 3 |
| 60 | 94 | 63 | 24 | 5 | 0 | 2 |

EXAMLE 4

Mixtures consisting of 45 grams of tungsten oxide and 7.0 grams of phosphoric acid having a purity of 85% were mixed with an aqueous mixture of aluminum ammonium sulfate dodecahydrate in amounts shown in Table 4, and then catalysts were produced from the respective mixtures by the same procedure as in Example 1.

Using these catalysts, the same reaction procedures as in Example 1 were repeated. The results are shown in Table 4.

Table 4

| No. | Quantity of Aluminum Ammonium Sulfate (g) | Atomic Ratio of Al/P | Yield of Maleic Anhydride (%) | | |
|---|---|---|---|---|---|
| | | | After 3 hours | After 30 hours | After 60 hours |
| 1 | 2.8 | 0.1 | 62 | 58 | 61 |
| 2 | 13.8 | 0.5 | 66 | 62 | 63 |
| 3 | 27.6 | 1.0 | 61 | 64 | 58 |
| 4 | 55.1 | 2.0 | 63 | 63 | 58 |

EXAMPLE 5

45 grams of tungsten oxide which was produced by the same method as in Example 1 was mixed with an aqueous mixture containing 7.0 grams of phosphoric acid having a purity of 85% and 1.5 grams of aluminum chloride hexahydrate to obtain a pastelike mixture. The pastelike mixture was molded, and then dried. The atomic ratio of phosphorus: tungsten: aluminum (P:W:Al) in the thus obtained catalyst was 1:3.2:0.1. The catalyst was further calcined in an air stream at a temperature of 500° C for 3 hours before using in the reaction.

Using the catalyst, the same reaction procedures as in Example 1 except that butadiene was used as the unsaturated hydrocarbon feed instead of butene-1 were repeated. The results are shown in Table 5.

Table 5

| Lapse of Time After Start of Reaction (hour) | Conversion of butadiene (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 97 | 66 | 15 | 10 | 4 | 2 |
| 15 | 97 | 65 | 16 | 11 | 3 | 2 |
| 60 | 98 | 63 | 16 | 13 | 3 | 3 |

EXAMPLE 6

45 grams of tungsten oxide which was produced by the same method as in Example 1 was mixed with an aqueous mixture containing 7.0 grams of phosphoric acid having a purity of 85% and 1.5 grams of aluminum chloride to obtain a pastelike mixture. The pastelike mixture was molded, and then dried. The atomic ratio of phosphorus: tungsten: aluminum (P:W:Al) in the thus obtained catalyst was 1:3.2:0.1. The catalyst was further calcined in the air stream at a temperature of 500° C for 3 hours before using in the reaction.

Using the catalyst, the same reaction procedures as in Example 1 except that mixed gas composed of 25 weight percents of butanes, 48 weight percents of n-butene and 27 weight percents of isobutene was used as the unsaturated hydrocarbon feed instead of butene-1. The yields of maleic anhydride after 3 hours, 30 hours and 300 hours from the start of reaction were 33%, 36% and 36%, respectively.

EXAMPLE 7

Catalysts (I)-(III) below were prepared in accordance with the same method as described in Example 1 from 45 grams of tungsten oxide, 7 grams of phosphoric acid having a purity of 85% and a catalyst promoter, each name and the amount of which are shown in Table 6.

Table 6

| Catalyst | Tungsten Oxide (g) | Phosphoric Acid Having a Purity of 85% (g) | Catalyst Promoter (g) |
|---|---|---|---|
| I | 45 | 7 | Nickel nitrate hexahydrate 1.8 |
| II | 45 | 7 | Stannic chloride pentahydrate 2.1 |
| III | 45 | 7 | Niobium pentoxide 1.6 |

Using catalysts (I)-(III), the same reaction procedures as in Example 1 were repeated. The results are shown in Table 7.

Table 7

| Catalyst | Conversion of Butene-1 (%) | | | Yield of Maleic Anhydride (%) | | |
|---|---|---|---|---|---|---|
| | After 3 Hours | After 15 Hours | After 60 Hours | After 3 Hours | After 15 Hours | After 60 Hours |
| I | 90 | 90 | 90 | 51 | 52 | 49 |
| II | 98 | 98 | 99 | 59 | 60 | 59 |
| III | 98 | 98 | 97 | 61 | 62 | 59 |

EXAMPLE 8

Catalysts (I)-(IX) below were prepared in accordance with the same method as described in Example 2 from 45 grams of tungsten oxide, 7 grams of phosphoric acid having a purity of 85% and a catalyst promoter, each name and the amount of which are shown in Table 8.

Table 8

| Catalyst | Tungsten Oxide (g) | Phosphoric Acid Having a Purity of 85% (g) | Catalyst Promoter (g) |
|---|---|---|---|
| I | 45 | 7 | Cobalt chloride hexahydrate 1.4 |
| II | 45 | 7 | Cobalt chloride 14.5 |
| III | 45 | 7 | Zirconium nitrate pentahydrate 2.6 |
| IV | 45 | 7 | Zirconium sulphate tetrahydrate 21.5 |
| V | 45 | 7 | Antimony sulphate 3.2 |
| VI | 45 | 7 | Antimony trichloride 1.4 |
| VII | 45 | 7 | Germanium oxide 0.63 |
| VIII | 45 | 7 | Lead nitrate 2.0 |
| IX | 45 | 7 | Arsenic pentoxide 1.4 |

Using catalysts (I)-(IX), the same reaction procedures as in Example 2 were repeated. The results are shown in Table 9.

Table 9

| Catalyst | Conversion of Butene-1 (%) | | | Yield of Maleic Anhydride (%) | | |
|---|---|---|---|---|---|---|
| | After 3 Hours | After 15 Hours | After 60 Hours | After 3 Hours | After 15 Hours | After 60 Hours |
| I | 98 | 99 | 100 | 64 | 60 | 60 |
| II | 97 | 98 | 98 | 62 | 66 | 64 |
| III | 96 | 94 | 91 | 64 | 58 | 58 |
| IV | 97 | 98 | 94 | 62 | 66 | 65 |
| V | 94 | 94 | 91 | 64 | 60 | 60 |
| VI | 97 | 98 | 94 | 62 | 66 | 65 |
| VII | 94 | 94 | 94 | 54 | 50 | 48 |
| VIII | 97 | 98 | 98 | 55 | 57 | 56 |
| IX | 90 | 92 | 91 | 50 | 48 | 48 |

EXAMPLE 9

Mixtures consisting of 45 grams of tungsten oxide and 7.0 grams of phosphoric acid having a purity of 85% were mixed with an aqueous mixture of ferric nitrate nonahydrate in amounts shown in Table 10, and then catalysts were produced from the respective mixtures by the same procedure as in Example 1.

Using these catalysts, the same reaction procedures as in Example 1 were repeated. The results are shown in Table 10.

Table 10

| No. | Quantity of Ferric Nitrate Nonahydrate (g) | Atomic Ratio of Fe/P | Yield of Maleic Anhydride (%) | | |
|---|---|---|---|---|---|
| | | | After 3 hours | After 30 hours | After 60 hours |
| 1 | 2.5 | 0.1 | 60 | 56 | 59 |
| 2 | 12.3 | 0.5 | 62 | 58 | 59 |
| 3 | 24.5 | 1.0 | 59 | 57 | 54 |
| 4 | 49.0 | 2.0 | 59 | 59 | 54 |

EXAMPLE 10

Using a catalyst which obtained by the same procedure as Example 5 except that 2.5g of ferric nitrate nonahydrate was used instead of 1.5g of aluminum chloride, the same reaction procedures as in Example 5 were repeated. The atomic ratio of phosphorus: tungsten: iron in thus obtained catalyst was 1:3.2:0.1. The results are shown in Table 11.

Table 11

| Lapse of Time After Start of Reaction (hour) | Conversions of butadiene % | Maleic Anhydride | Yield (%) Carbon Monoxide | Carbon Dioxide | Acetic Acid | Compounds |
|---|---|---|---|---|---|---|
| 3 | 95 | 62 | 16 | 11 | 3 | 3 |
| 15 | 95 | 61 | 17 | 12 | 3 | 2 |
| 60 | 96 | 59 | 17 | 14 | 4 | 2 |

EXAMPLE 11

A catalyst which was obtained by the same procedure as in Example 5 was packed in a reactor having an inner diameter of 15 millimeters and a length of 600 millimeters. The reactor was equipped with means for heating the reactor and a sprayer adapted to spray an aqueous solution of triammonium phosphate into the reactor. Air containing 1 volume percent of butene-1 was introduced into the reactor at a space velocity of 3000 per hour, and an aqueous solution containing 10 weight percent of triammonium phosphate was sprayed into the reactor at a rate of 2 grams per day. The yield of maleic anhydride after 3 hours, 30 hours and 300 hours was 66%, 66% and 64%, respectively.

COMPARATIVE EXAMPLE 1

45 grams of tungsten oxide which was manufactured by the same procedure as in Example 1 were mixed with 7.0 grams of phosphoric acid having a purity of 85% and sufficient water to obtain a pastelike mixture and then the mixture was subjected to the same procedure as in Example 1. In the catalyst thus obtained, the atomic ratio of phosphorus: tungsten (P:W) was 1:3.2. The catalyst was further calcined in an air stream at a temperature of 500° C for 2 hours before using it in the reaction.

The thus obtained catalyst was packed in the same reactor as used in Example 1. Maintaining the highest temperature in the catalyst layer at 460° C, air containing one volume percent of butene-1 was introduced into the reactor at a space velocity of 3000 per hour. As a result, the yields of maleic anhydride and saturated acid were respectively 60% and 1%, and the conversion of butene-1 was 98%.

The deterioration in yield of maleic anhydride during the course of the reaction is shown in Table 12.

Table 12

| Lapse of Time After Start of Reaction (hour) | Conversion of butene-1 (%) | Yield (%) | | | | |
|---|---|---|---|---|---|---|
| | | Maleic Anhydride | Carbon Monoxide | Carbon Dioxide | Acetic Acid | Aldehyde Compounds |
| 3 | 98 | 62 | 26 | 9 | 0 | 1 |
| 15 | 94 | 45 | 33 | 14 | 1 | 1 |
| 60 | 94 | 28 | 42 | 19 | 1 | 4 |

COMPARATIVE EXAMPLE 2

Mixtures consisting of 45 grams of tungsten oxide and 5.3 grams of phosphoric acid having a purity of 85% were mixed with 35 ml of concentrated hydrochloric acid containing 1.6g of vanadium pentoxide, and then catalysts were produced from the respective mixtures by the same procedure as in Example 1.

Using these catalysts, the same reaction procedure as in Example 1 was repeated. The results are shown in Table 13.

Table 13

| Lapse of Time After Start of Reaction (hour) | Conversion of butene-1 (%) | Yield (%) | | | |
|---|---|---|---|---|---|
| | | Maleic Anhydride | Carbon Monoxide | Carbon Dioxide | Acetic Acid |
| 3 | 100 | 44 | 36 | 18 | 2 |
| 15 | 100 | 45 | 37 | 16 | 2 |
| 60 | 100 | 45 | 37 | 16 | 2 |

What is claimed is:

1. A method for preparing maleic anhydride which comprises oxidizing in the vapor phase an unsaturated hydrocarbon selected from the group consisting of butene-1, butene-2, butadiene, cyclopentadiene, pentene-1, mixtures thereof and $C_4$-fractions obtained by naphtha cracking in a reaction zone at a temperature of from 250° to 650° C, in the presence of a catalyst consisting essentially of the oxides of tungsten and phosphorous of a metallic element belonging to groups III-A, III-B, IV-A and VIII of the periodic table, arsenic, zirconium, antimony and niobium.

2. A method according to claim 1 wherein the metallic element of the catalyst promoter belongs to the groups III A or III B of the Periodic Table.

3. A method according to claim 1, wherein a phosphorus compound is introduced into the reaction zone.

4. A method according to claim 1 wherein the catalyst is supported on a carrier.

5. A method according to claim 2, wherein a phosphorus compound is introduced into the reaction zone.

6. A method according to claim 2 wherein the catalyst is supported on a carrier.

7. A method according to claim 1 wherein the atomic ratio of tungsten to phosphorus is less than 30.

8. A method according to claim 1 wherein oxidation is effected by admixing said unsaturated hydrocarbon with an oxidizing agent comprising oxygen or an oxygen-containing gas.

9. A method according to claim 8 wherein the molar ratio of unsaturated hydrocarbon to oxygen is less than 1/10 or more than ½.

10. A method according to claim 1 wherein the gaseous hourly space velocity through the reaction zone ranges from 500 to 15,000 per hour.

* * * * *

PO-1050
(5/69)

UNITED STATES PATENT OFFICE
CERTIFICATE OF CORRECTION

Patent No. 4,003,920                  Dated  January 18, 1977

Inventor(s) Ryuhei Ueeda

It is certified that error appears in the above-identified patent and that said Letters Patent are hereby corrected as shown below:

IN THE CLAIMS:

Claim 1, line 9, after "phorous" and before "of", insert --and at least one catalyst promoter selected from the group consisting of a compound--.

Signed and Sealed this

Third Day of May 1977

[SEAL]

Attest:

RUTH C. MASON
Attesting Officer

C. MARSHALL DANN
Commissioner of Patents and Trademarks